US010028754B2

United States Patent
Johnson et al.

(10) Patent No.: US 10,028,754 B2
(45) Date of Patent: Jul. 24, 2018

(54) MEDICAL IMPACTOR TOOL

(71) Applicant: TTI (Macao Commercial Offshore) Limited, Macau (MO)

(72) Inventors: Henry Thomas Johnson, Seneca, SC (US); Brian Albert Williams, Clemson, SC (US); Isiah Daniel Smith, Greenville, SC (US); Christopher Pedicini, Nashville, TN (US)

(73) Assignees: TTI (MACAO COMMERCIAL OFFSHORE) LIMITED, Macau (MO); MEDICAL ENTERPRISES, LLC, Norcross, GA (US)

( * ) Notice: Subject to any disclaimer, the term of this patent is extended or adjusted under 35 U.S.C. 154(b) by 291 days.

(21) Appl. No.: 14/806,337

(22) Filed: Jul. 22, 2015

(65) Prior Publication Data

US 2017/0020536 A1    Jan. 26, 2017

(51) Int. Cl.
  *A61B 17/16*  (2006.01)
  *A61B 17/92*  (2006.01)
  *A61B 17/00*  (2006.01)

(52) U.S. Cl.
  CPC ........ *A61B 17/1659* (2013.01); *A61B 17/164* (2013.01); *A61B 17/1626* (2013.01); *A61B 17/92* (2013.01); *A61B 17/1624* (2013.01); *A61B 17/1628* (2013.01); *A61B 17/1668* (2013.01); *A61B 2017/00132* (2013.01); *A61B 2017/00367* (2013.01); *A61B 2017/00393* (2013.01)

(58) Field of Classification Search
  CPC . A61B 17/1659; A61B 17/1668; A61B 17/92; A61B 2017/922
  See application file for complete search history.

(56) References Cited

U.S. PATENT DOCUMENTS

| 5,057,112 | A | * | 10/1991 | Sherman | ............ A61B 17/1604 606/100 |
|---|---|---|---|---|---|
| 7,320,368 | B2 | | 1/2008 | Watanabe | |
| 7,513,402 | B2 | | 4/2009 | Miyashita et al. | |
| 7,845,426 | B2 | | 12/2010 | Jung et al. | |
| 8,191,648 | B2 | | 6/2012 | Watanabe et al. | |
| 8,393,409 | B2 | * | 3/2013 | Pedicini | ................ A61B 17/92 173/109 |
| 8,936,105 | B2 | * | 1/2015 | Pedicini | ............. A61B 17/1604 173/114 |
| 8,936,106 | B2 | * | 1/2015 | Pedicini | ............. A61B 17/1626 173/109 |
| 2006/0185865 | A1 | * | 8/2006 | Jung | .................... B25D 16/006 173/48 |

(Continued)

FOREIGN PATENT DOCUMENTS

| CA | 2823207 | 7/2012 |
|---|---|---|
| CA | 2872180 | 11/2013 |

(Continued)

*Primary Examiner* — Eric S Gibson

(74) *Attorney, Agent, or Firm* — Michael Best & Friedrich LLP

(57) ABSTRACT

A power tool includes an output member, a drive mechanism operable to perform work on the output member in one of a first mode or a second mode, and an actuator for activating the drive mechanism in the first mode or the second mode based upon an amount of time the actuator is depressed.

10 Claims, 2 Drawing Sheets

(56) References Cited

U.S. PATENT DOCUMENTS

| | | | |
|---|---|---|---|
| 2006/0278680 A1* | 12/2006 | Viola | A61B 17/07207 227/176.1 |
| 2010/0282483 A1 | 11/2010 | Jung et al. | |
| 2011/0064978 A1* | 3/2011 | McGahan | A61B 17/7091 429/61 |
| 2012/0172939 A1* | 7/2012 | Pedicini | A61B 17/1604 606/86 R |
| 2012/0215267 A1* | 8/2012 | Pedicini | A61B 17/92 606/86 R |
| 2013/0161050 A1* | 6/2013 | Pedicini | B25D 17/00 173/201 |
| 2013/0186666 A1 | 7/2013 | Yoshino et al. | |
| 2014/0100687 A1 | 4/2014 | Ekstrom et al. | |
| 2014/0142583 A1* | 5/2014 | Fortin | A61B 17/1604 606/100 |
| 2014/0318819 A1* | 10/2014 | Pedicini | A61B 17/1626 173/2 |
| 2014/0318823 A1* | 10/2014 | Pedicini | A61B 17/1604 173/201 |
| 2015/0196343 A1* | 7/2015 | Donald | A61B 17/92 606/100 |
| 2016/0199199 A1* | 7/2016 | Pedicini | A61F 2/4603 606/100 |
| 2017/0020536 A1* | 1/2017 | Johnson | A61B 17/1626 |
| 2017/0224400 A1* | 8/2017 | Mistry | A61B 18/00 |

FOREIGN PATENT DOCUMENTS

| | | |
|---|---|---|
| CA | 2872182 | 11/2013 |
| EP | 2684529 | 1/2014 |

* cited by examiner

MEDICAL IMPACTOR TOOL

FIELD OF THE INVENTION

The invention relates to power tools, and more particularly to operational methods for power tools.

SUMMARY OF THE INVENTION

The invention provides, in one aspect, a power tool including an output member, a drive mechanism operable to perform work on the output member in one of a first mode or a second mode, and an actuator for activating the drive mechanism in the first mode or the second mode based upon an amount of time the actuator is depressed.

The invention provides, in another aspect, a method for operating a power tool including actuating a switch of the power tool to initiate activation of a drive mechanism, maintaining the switch in an actuated state for a predetermined amount of time or less to operate the drive mechanism in a first mode, and maintaining the switch in the actuated state for more than the predetermined amount of time to operate the drive mechanism in a second mode.

Other features and aspects of the invention will become apparent by consideration of the following detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

Figure 1:
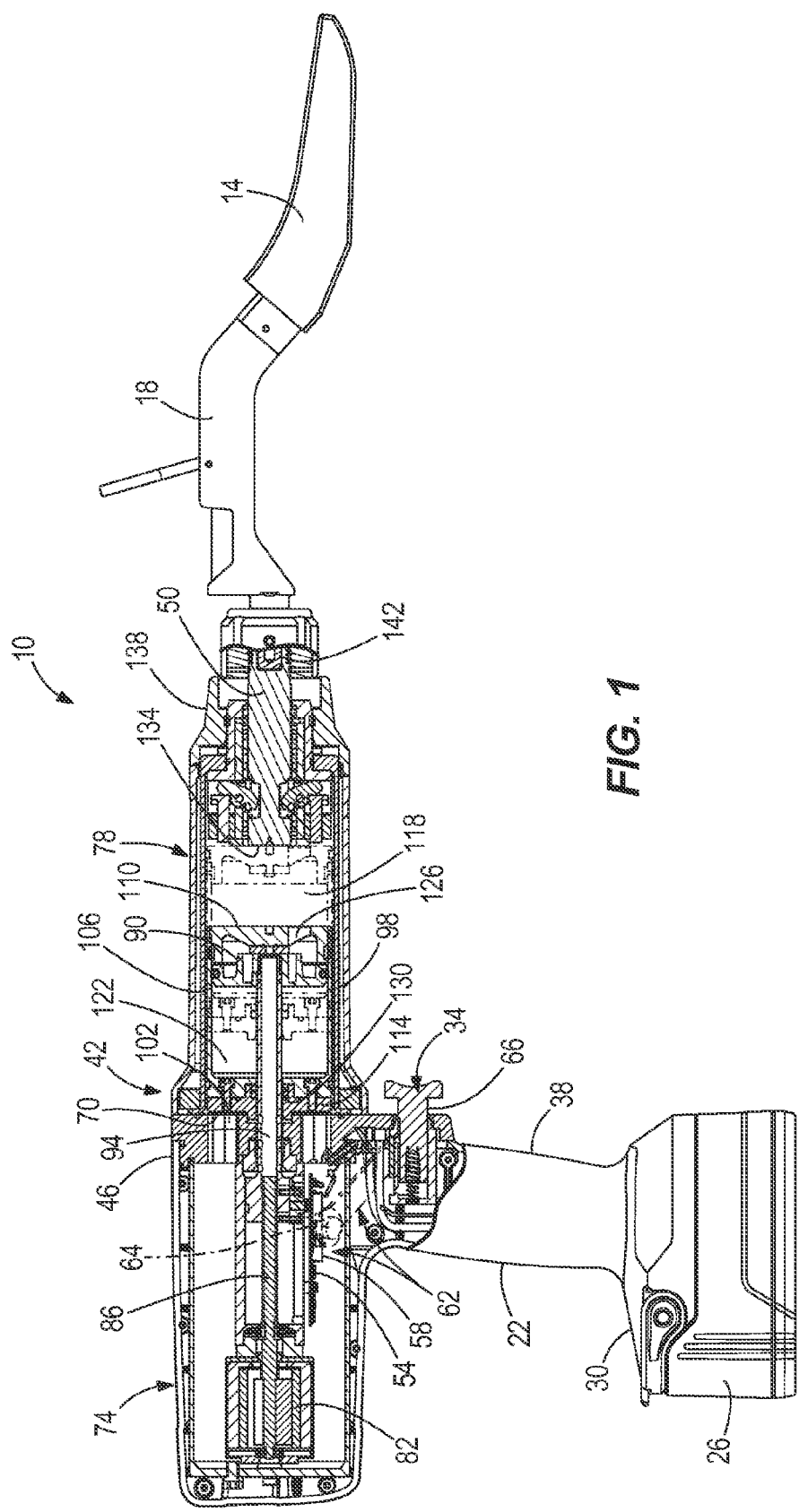
FIG. 1 is a cross-sectional plan view of a power tool in accordance with an embodiment of the invention.

FIG. 1 illustrates a power tool, such as a medical impactor 10, coupled to a tool bit (e.g., a rasp or broach 14) by an adapter 18. As is explained in further detail below, the impactor 10 delivers axial impacts to the adapter 18 and the broach 14 during a surgical procedure, such as preparing the femoral canal for an orthopedic implant during a hip replacement procedure. The impactor 10 includes a housing 22, a battery 26 coupled to a battery support portion 30 of the housing 22, an actuator 34 positioned adjacent a handle portion 38 of the housing 22, and a drive mechanism 42 supported within a barrel portion 46 of the housing 22. The impactor 10 also includes an output member 50 that is impacted by the drive mechanism 42. The impacts upon the output member 50 are subsequently transferred to the adapter 18 and the broach 14. In some embodiments of the impactor 10, the adapter 18 may be omitted and the output member 50 may directly interface with the broach 14 for delivering impacts thereto.

With continued reference to FIG. 1, the battery support portion 30 extends from the handle portion 38 and is configured to detachably couple the battery 26, such as a lithium ion power tool battery pack. The battery support portion 30 includes electrical contacts and a latching mechanism for mechanically interlocking the battery 26 with the battery support portion 30. The actuator 34 is capable of selectively electrically connecting the battery 26 to the drive mechanism 42 via a printed circuit board 54 (PCB) and a microcontroller 58 on the PCB 54. In the illustrated embodiment of the impactor 10, the actuator 34 includes magnetic switch 62 having sensor, such as a Hall-effect sensor, for detecting displacement of a magnet 64. A trigger 66 extends from the handle portion 38 of the housing 22 to which the magnet 64 is coupled for movement therewith. The trigger 66 is graspable and depressible by a user of the impactor 10 in order displace the magnet 64 relative to the Hall-effect sensor on the PCB 54 to operate the switch 62.

In the illustrated embodiment of the impactor 10, the drive mechanism 42 includes a plate 70 dividing the barrel portion 46 of the housing 22 into a rear cavity 74 and a front cavity 78, a motor 82 positioned within the rear cavity 74, and a screw drive 86 that extends through the plate 70 into the front cavity 78. Within the front cavity 78, the drive mechanism 42 also includes a piston 90 attached to an output shaft 94 of the screw drive 86 and a movable cylinder 98 within which the piston 90 is located. As described in more detail below, the piston 90 is axially displaceable within the movable cylinder 98 in order to generate a vacuum within the movable cylinder 98. The movable cylinder 98 is selectively retained to the plate 70 by a latch 102 (e.g., a magnetic latch, a ball detent, etc.).

The movable cylinder 98 includes a sleeve 106, a front cap 110 attached to a front end of the sleeve 106, and a rear cap 114 attached to a rear end of the sleeve 106. As a result of the piston 90 being movable within and relative to the movable cylinder 98, a first variable volume 118 is defined within the movable cylinder 98 between the piston 90 and the front cap 110. Likewise, a second variable volume 122 is defined within the movable cylinder 98 between the piston 90 and the rear cap 114. The front cap 110 includes an aperture 126 to fluidly interconnect the first variable volume 118 with the atmosphere. Therefore, the static pressure within the first variable volume 118 is nominally equal to atmospheric pressure at all times during operation of the impactor 10. The rear cap 114, however, includes a one-way valve 130 that seals the second variable volume 122 during an extension stroke of the piston 90 within the movable cylinder 98 to create a vacuum in the second variable volume 122. During a retraction stroke of the piston 90, the one-way valve 130 permits air to be exhausted from the second variable volume 122 to the atmosphere. During a subsequent extension stroke of the piston 90, the one-way valve 130 again seals the second variable volume 122 to generate the vacuum within the second variable volume 122.

With continued reference to FIG. 1, the output member 50 includes a first impact face 134 within the front cavity 78, and extends through the front cavity 78 into a chuck 138 of the impactor 10. The output member 50 also includes a second impact face 142 in facing relationship with a portion of the adapter 18 for impacting it during operation of the impactor 10.

Prior to initiating an impact operation, the piston 90 and the movable cylinder 98 each assume a fully retracted "home" position (the movable cylinder 98 being shown in the home position in FIG. 1), with the rear cap 114 of the movable cylinder 98 being held adjacent the plate 70 by the latch 102. To initiate an impact operation, the switch 62 is actuated (e.g., by depressing the trigger 66), thereby activating the motor 82 of the drive mechanism 42 (via the microcontroller 58) to rotate in a first direction. When the motor 82 rotates in the first direction, the screw drive 86 is extended to displace the piston 90 toward an extended position within the movable cylinder 98 (shown in FIG. 1), which generates a vacuum within the second variable volume space 122 of the movable cylinder 98 until a predetermined vacuum in the second variable volume space 122 is reached. At this time, the latch 102 releases the movable cylinder 98, and a pressure differential acting on the movable cylinder 98 accelerates it toward the output member 50. Upon the movable cylinder 98 reaching its extended position, the front cap 110 of the cylinder 98 strikes the first impact face 134 of the output member 50 so as to transmit an impact force to the output member 50. The direction of rotation of the motor 82 is then reversed, operating the screw drive 86 in a reverse direction to retract the piston 90 toward its home position and the plate 70, pulling the movable cylinder 98 with it, until both the piston 90 and the movable cylinder 98 reach their respective home positions. At this time, the movable cylinder 98 is re-latched into a locked state prior to starting another drive cycle. During subsequent drive cycles, the movable cylinder 98 is reciprocated in the manner described above to impart axial impacts upon the output member 50.

Figure 2:
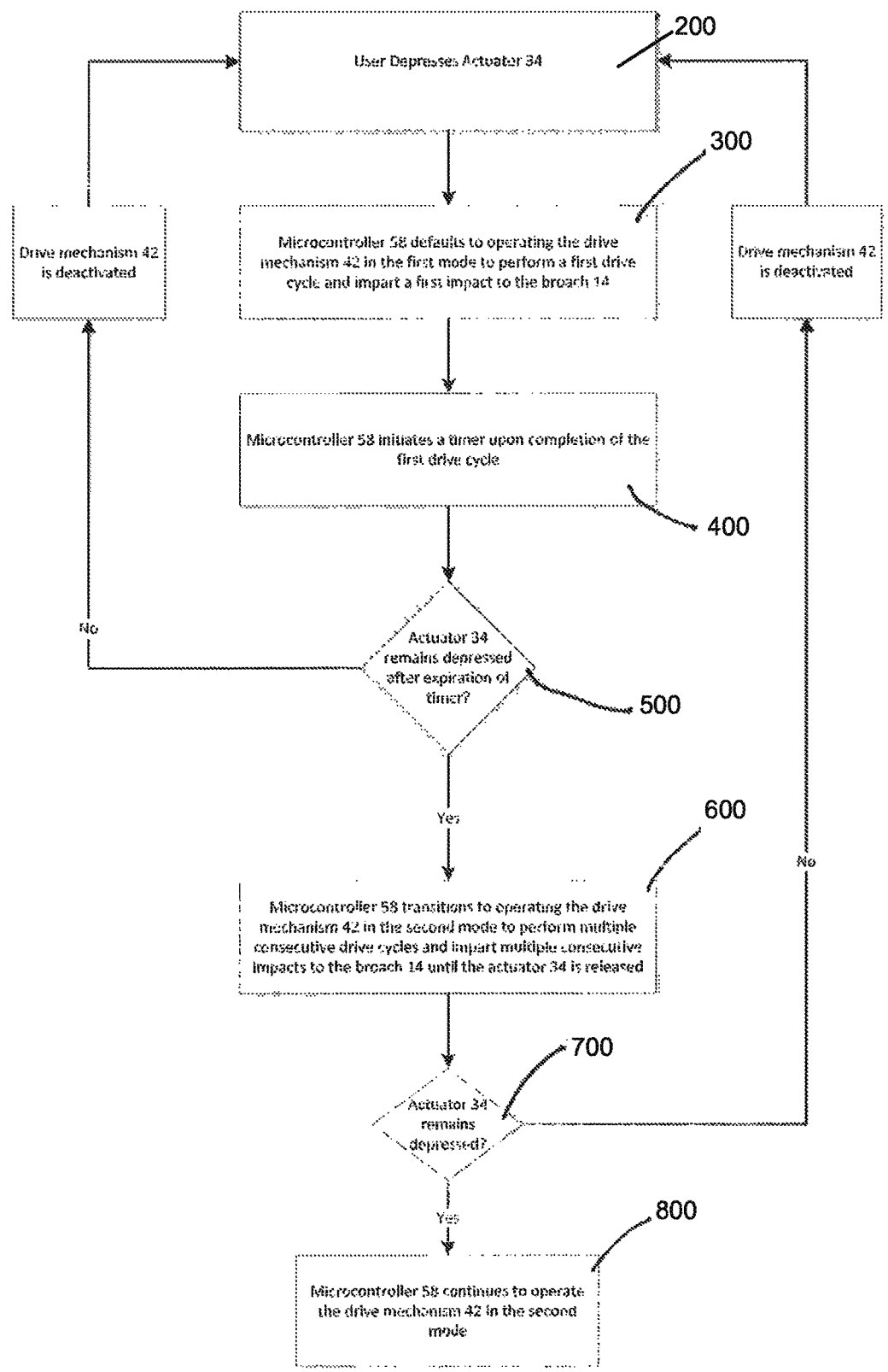
FIG. 2 is a flow chart illustrating a method of operating the power tool of FIG. 1.

As illustrated in FIG. 2, the drive mechanism 42 is operable in either a first mode or a second mode based on an amount of time the actuator 34 is depressed by the user. At step 200, the user depresses the actuator 34, at which point the microcontroller 58 defaults to operating the drive mechanism 42 in the first mode (step 300). In the first mode or single impact mode, the drive mechanism 42 is activated to complete a single drive cycle to generate a single impact on the output member 50, and subsequently on the broach 14. At step 400, the microcontroller 58 initiates a timer when the movable cylinder 98 is detected in the "home" position (e.g., by the latch 102) after a single drive cycle has been completed. After expiration of the timer, the microcontroller 58 determines if the actuator 34 remains depressed (step 500). As illustrated in FIG. 2, if the actuator 34 is not depressed, the drive mechanism 42 is deactivated. The user may use the impactor 10 to perform multiple consecutive single-impact cycles (i.e., activate the drive mechanism 42 in the first mode) by depressing the actuator 34 multiple times, but then releasing the actuator 34 before the time delay has passed (i.e., the timer has expired) in each instance. This may be useful, for example, when a surgeon is attempting to precisely prepare or finalize preparation of the femoral canal of a patient.

Alternatively, as seen in step 600, if the actuator 34 remains depressed after expiration of the timer, the microcontroller 58 transitions to operating the drive mechanism 54 from the first mode to the second mode. In the second mode or multi-impact mode, the drive mechanism 42 performs multiple consecutive drive cycles and imparts multiple consecutive impacts on the output member 50 (and therefore the broach 14) until the actuator 34 is released. At step 700, the microcontroller 58 monitors the status of the actuator 34 to confirm that it remains depressed. If the actuator 34 remains depressed, the microcontroller 58 continually operates the drive mechanism 54 in the second mode (step 800). If the actuator 34 is released, the drive mechanism 54 is deactivated and the process shown in FIG. 2 is reset to step 200. The second mode is particularly useful, for example, when a surgeon is initially attempting to compact bone within the femoral canal well before attempting to seat an implant.

As illustrated in FIG. 2, the drive mechanism 42 is initially operated in the first mode in response to initial actuation of the actuator 34, and may or may not transition into the second mode based on the amount of time the actuator 34 is maintained in the actuated state. The time delay is sufficiently long to permit the user to release the trigger 66 before the time delay expires, thus enabling the impactor 10 to deliver a single impact to the broach 14, while also not being too long so as to introduce a perceptible delay between the first and second impacts applied to the broach 14 when the drive mechanism 42 transitions from operating in the first mode to the second mode. The time delay may be, for example, approximately 100 to 200 milliseconds.

Various features of the invention are set forth in the following claims.

What is claimed is:
1. A power tool comprising:
an output member;
a drive mechanism operable to perform work on the output member in one of a first mode or a second mode; and
an actuator for activating the drive mechanism in the first mode or the second mode based upon an amount of time the actuator is depressed;
wherein, in the first mode, the drive mechanism is operated for only a single drive cycle, and in the second mode, the drive mechanism is operated continuously until the actuator is released.
2. The power tool of claim 1, wherein the first mode is a single impact mode and the second mode is a multi-impact mode.
3. The power tool of claim 1, wherein, upon activation, the drive mechanism is initially operated in the first mode through a predetermined amount of time of the actuator being depressed, after which the drive mechanism transitions from operating in the first mode to the second mode.
4. The power tool of claim 1, wherein the drive mechanism includes
a motor;
a screw drive operated by the motor in a reciprocating manner; and
a piston coupled to an output of the screw drive.
5. The power tool of claim 4, wherein the drive mechanism further includes a movable cylinder driven by the piston in a reciprocating manner for impacting the output member.
6. The power tool of claim 5, wherein the piston is located within the movable cylinder, and wherein the piston is driven in a forward direction to generate a vacuum within the movable cylinder, which accelerates the movable cylinder toward the output member.
7. The power tool of claim 6, wherein the movable cylinder is held in a fixed position until a predetermined vacuum is reached therein, after which the movable cylinder is released and accelerated toward the output member.
8. The power tool of claim 1, wherein the amount of time is between 100 milliseconds and 200 milliseconds.
9. The power tool of claim 1, further comprising a broach coupled to the output member.
10. The power tool of claim 1, wherein the actuator includes a magnetic switch.

* * * * *